United States Patent [19]

Lindblom et al.

[11] Patent Number: 4,929,443
[45] Date of Patent: May 29, 1990

[54] METHOD OF TREATING INTERFERON SENSITIVE DISEASES, AND A METHOD AND DEVICE FOR PREPARING γ-INTERFERON CONTAINING PREPARATION

[76] Inventors: Ragnvald E. Lindblom, Alsäter, S-740 10 Almunge; Ulf S. Rothman, Box 120, S-230 10 Skanör, both of Sweden

[21] Appl. No.: 50,470

[22] Filed: May 18, 1987

Related U.S. Application Data

[63] Continuation of Ser. No. 711,567, Feb. 13, 1985, abandoned, which is a continuation of Ser. No. 503,575, Jun. 13, 1983, abandoned.

[51] Int. Cl.$^5$ .................... A61K 45/02; C12P 21/00
[52] U.S. Cl. ............................ 424/85.5; 435/70.4; 435/70.5
[58] Field of Search ................ 424/85.5; 435/68

[56] References Cited

U.S. PATENT DOCUMENTS 4,382,027 3/1983 Braude .................................. 424/85

4,490,357 12/1984 Skurkovich et al. ................ 424/85

OTHER PUBLICATIONS

Skurkovich, et al., Bomedicine, vol. 29, pp. 227–228, 1978.
O'Malley, J.; Methods in Enzymology, vol. 78, pp. 540–545, Academic Press, 1981.
Osther, K., et al., The Biology of the Interferon System E. De Maeyes and H. Schellekens, ed., pp. 527–533, 1963.

*Primary Examiner*—Blondel Hazel
*Attorney, Agent, or Firm*—Bacon & Thomas

[57] ABSTRACT

Methods and means for treating interferon-sensitive diseases are disclosed, wherein a whole blood sample is taken from a patient suffering from such disease and is incubated in vitro together with a mitogen to produce γ-interferon. After incubation the whole blood sample is subjected to a separation step for producing a blood plasma product, which is free from the mitogen but contains γ-interferon. This blood plasma product is used for re-administration to the patient from which the whole blood sample was taken.

6 Claims, No Drawings

METHOD OF TREATING INTERFERON SENSITIVE DISEASES, AND A METHOD AND DEVICE FOR PREPARING γ-INTERFERON CONTAINING PREPARATION

This application is a continuation of application Ser. No. 711,567, filed Feb. 13, 1985 now abandoned, which is a continuation of Ser. No. 503,575, filed June 13, 1983, now abandoned.

The present invention relates to a novel method of producing interferon, a novel method of treatment for preventing and treating interferon sensitive diseases and novel means for carrying out these methods.

Interferons are proteinaceous substances which are induced intra cellularly or extra cellularly upon exposure of the cells to interferon inducing agents such as viruses, bacteria, protozoes, rickettsia, nucleic acids, endotoxines, polysaccharides, etc.

Interferons have a great potential interest as drugs since they unspecifically inhibit the growth of various viruses in the cells, have an antitumour effect on non-viral or viral tumours, etc.

However, the development of interferon as a drug is severely inhibited by the great difficulties in preparing the necessary amounts, i.a. depending on the fact that interferon is species specific. Thus, only interferon originating from live human cells is useful for human therapy. For the preparation of interferon human leukocytes and the like are conventionally used, and the very limited supply of such starting material is a great problem in view of the small amounts which can be prepared.

Attempts have also been made to prepare interferon in vitro by culturing established human cells on a nutrient medium in the presence of various interferon inducers. However, not either this method has given the desired results.

In recent years it has been established that human interferon exists in at least three different molecular variants, viz. α-interferon (previously called leukocyte interferon), β-interferon (previously fibroblast interferon), and γ-interferon (previously immune interferon).

It is further known from numerous publications that many substances induce the formation of interferons. Thus, α- and β-interferon are induced by viruses, and γ-interferon by so called mitogens and antigens.

γ-interferon is believed to have a tremendous potential as an agent for treating interferon-sensitive diseases, such as tumours. However, γ-interferon is difficult to produce and is unstable, and attempts to stabilize it have so far been unsuccessful.

The present invention suggests a new approach to the problem of preparing and using γ-interferon for treating interferon-sensitive diseases. A first aspect of the invention is based on the per se well known fact that mitogens induce the production of γ-interferon, and in accordance with this aspect of the invention γ-interferon production is induced by incubating whole blood samples from a patient to be treated with one or more mitogens in vitro. After the incubation has been terminated the incubated blood sample is subjected to a separation step to produce a plasma containing the interferon produced but not the mitogen. The incubation and separation steps are performed in vitro.

In a second aspect of the invention the (γ)interferon-containing plasma is then re-administered to the same patient, who will thus receive an interferon preparation which does not only originate from the same species (a human) but from the same individual (himself/herself): the preparation is "individual specific". This procedure offers a plurality of important advantages, i.a. the following: a very simple, rapid and inexpensive production of the preparation, elimination or considerable reduction of the instability problems with γ-interferon, reduced side effects because of the individual specificity, etc.

It is essential to separate the mitogen before re-administering the interferon containing plasma to the patient. For this separation any suitable conventional separation technique can be used, provided that the same is capable of separating all of the mitogen from the plasma product while leaving a therapeutically effective amount of the produced interferon therein. The separation technique can be based on the physical and/or biological/biochemical properties of the mitogen. Examples of suitable separation techniques are affinity chromatography, e.g. using biothine, and ultrafiltration, the latter technique being described in some detail below as an illustrative example only.

When using ultrafiltration the cut-off properties of the ultra filter are chosen with regard to the choice of the γ-interferon inducing mitogens. Thus, the filter and the mitogens should be chosen such that γ-interferon can pass through the filter, whereas the mitogens are excluded, or vice versa. Since the major part of γ-interferon has a molecular weight of about 20,000–75,000 (with a minor part having a molecular weight of about 65,000–70,000) the filter should permit substances of a molecular weight of up to about at least 50,000 to pass through, when the mitogen has a molecular weight which is higher than that of the interferon. The upper cut-off limit is chosen with regard to the molecular weight of the mitogen used. Obviously the mitogen must in this case have a molecular weight of at least about 50,000. Preferred mitogens are phytohemagglutinin (PHA) and concanvaline-A (con-A). PHA has a molecular weight of about 127,000, thus permitting a cut-off value of the filter of e.g. about 100,000, which also permits the minor part (see above) of γ-interferon to pass through the filter. Mitogens having comparatively low molecular weights, e.g. overlapping the molecular weight range for the interferon, can be bound to a suitable matrix to increase the molecular weight and permit separation by ultrafiltration. As mentioned above low molecular mitogens can be separated by using a filter having a low cut-off limit permitting the mitogen, but not the interferon to pass through.

Mitogens having lower molecular weights can also be used when separating the mitogen by other techniques than filtration. A preferred mitogen of this molecular weight size is Staf. enterotoxin.

The incubation of the whole blood sample with the mitogen (or mitogens) is carried out under conditions promoting γ-interferon production, e.g. at a temperature of about 35° to 40° C. and for e.g. at least about 2 or 4 hours (up to several days). The amount of mitogen to be used depends on the specific mitogen. This amount is chosen so as to produce an optimal amount of γ-interferon, and it can easily be established by a person of average skill in the art by simple tests. Excessive amounts of mitogen should be avoided since this may inhibit the interferon production. For the preferred mitogen PHA suitable amounts are e.g. from about 1 to about 5 μg PHA per ml whole blood sample.

The whole blood sample is preferably taken by means of a specially prepared sterile test tube which can be provided with a needle for taking a blood sample directly from the patient to the tube. Such a test tube—which is preferably heparinized or provided with any other suitable anti-coagulant and contains an efficient amount of one or more mitogens—is also an object of the present invention. The incubated blood sample is preferably centrifuged before the separation step, especially the filtering step, in order to prevent clotting of the filter by erythrocytes etc. The filter may be provided in the test tube, or the separation may be performed using separate separation means such as an ultrafiltration apparatus.

The preferred mode of administering the interferon-containing preparation is by intramuscular injection, but also other routes may be possible, such as intravenous or subcutaneous injection. Where combined treatment with a histamine H2-antagonist is used, the histamine H2-antagonist may be injected together with the γ-interferon-containing plasma or it may be administered separately, e.g. by the oral route. The dosage of the histamine H2-antagonist will vary depending on the chosen compound, the condition of the patient, etc. As a thumb rule one can use dosages of the same order as those used when treating e.g. peptic ulcer with the histamine H2-antagonist alone, these dosages being well known.

It is believed that the effect obtained by means of the interferon preparation and treatment in accordance with the invention is a result both of the direct effect of γ-interferon as such and on the fact that γ-interferon triggers the production of α- and β-interferon in vitro and/or in vivo. It may in this context be mentioned that α- and β-interferon are capable of passing through the filter together with γ-interferon (when using this separation technique). The incubation of the whole blood sample with the mitogen also triggers the production of other lymphokines, which further enhance the effect of the γ-interferon-containing blood plasma. In particular the triggered production of interleukins, especially interleukin II (ILII), is believed to give a valuable contribution in the treatment of the above mentioned diseases. Such lymphokins, especially ILII, can readily be separated from the mitogen in the separation step, together with the interferons. For example, ILII has a suitable molecular weight somewhat lower than that of γ-interferon.

In a further aspect of the invention the interferon-containing plasma is administered in combination with a histamine H2-antagonist. As is well known, histamine H2-antagonists are compounds which block histamine H2-receptors. Histamine H2-antagonists are useful i.a. for the treatment of peptic ulcer. The most well known histamine H2-antagonist is cimetidine (N-cyano-N'-methyl-N''-(2-[[(5-methyl-1H-imidazol-4-yl)methyl]thio]ethyl]guanidine), but a great number of other histamine H2-antagonists have been described. According to this further aspect of the invention it has unexpectedly been found that a synergistic effect, in particular a synergistic anti-tumour effect, is achieved when γ-interferon is administered together with a histamine H2-antagonist such as cimetidine. The mechanism of this synergistic effect has not been clarified.

The following test procedures were carried out in order to verify the operativeness of the method according to the invention. The Examples are given for illustrative purposes only, and they are not intended to limit the scope of the invention.

EXAMPLE 1

5 ml of human whole blood were collected in a sterile heparinized (as an anti-coagulant) plastic vacuum tube containing 15 μg PHA (3 μg/ml blood sample) and incubated at 37° C. on a water bath for at least 4 h. The tube was then centrifuged and the supernatant plasma collected (about 2.5 ml). The collected plasma was then, still under sterile conditions, ultrafiltrated through an Amicon Diaflo filter. Two types of this filter were used, viz. the XM 50 type and the XM 100A type, having cut-off limits of 50,000 and 100,000 respectively. This means that molecules having a molecular weight up to about 50,000 and 100,000 respectively can pass through the filter, whereas larger molecules are excluded.

The ultrafiltrate obtained was tested as to interferon activity in the so-called NK system (as described by Ratliff et al in Cellular Immunology, Vol. 57, Jan. 1, 1981) with the use of target cell K 562 erythroid cell line. It was found that the ultrafiltrate exhibited NK acitivity even after so high dilution as 1:10,000. A 100% increase compared to the normal value was observed as the highest NK activity. No mitogen (PHA) could be detected in any of the tested ultrafiltrates, and no difference was found between the ultrafiltrates from the two filters (XM 50 and XM 100A).

EXAMPLE 2

PHA in varying amounts was added to 10 ml of heparinized peripheral blood, mixed well and incubated for 4 hrs at 37° C. The blood cells were separated from plasma by centrifugation, and the plasma was ultrafiltrated through Amicon filters with a cut off of MW. 50,000. Filtered plasma was tested for capacity to stimulate the NK (natural killer) activity of mononuclear blood or spleen cells as an indicator of the presence of gamma-interferon. The test was a standard test for NK lymphocyte activity making use of target cells from a very sensitive cell line (K 562 erythroblastoid cells), labelled with $^{51}$Cr. Mononuclear cells of healthy human donor were incubated for 2 hrs at 37° C. with plasma to be tested for interferon content, after which the cells were added to K 562 target cells at various ratios and incubated for 4 hrs. The released radioactivity was measured in a gamma counter as a measure of the extent of cytolytic effects on the target cells.

Results of this test are given in Table 1, from which it can be seen that plasma of heparinised human blood which has been incubated for 4 hrs with 2 or 8 μg PHA per ml leads to approximately a doubling of the NK activity when tested at dilution 1:30 and 1:100 and compared to plasma of similarly incubated blood without added PHA. Similar tests, but using rat blood instead of human blood samples demonstrated a stimulated NK activity of spleen lymphocytes exposed to plasma diluted 1:30, 1:100, 1:1000 and 1:10,000.

EXAMPLE 3

γ-interferon-containing rat plasma was prepared as in Example 2, using PHA (available from Pharmacia AB, Uppsala, Sweden) as the mitogen. The γ-interferon preparation was injected intramuscularly (21 doses of 0.1–0.4 ml per animal) in combination with a histamine H2-antagonist (cimetidine) to rats which had been challeged subcutaneously with a transplantable DMH-induced colon carcinoma isograft ($1.5 \times 10^3$ viable cells). The rejection of colon cancer isograft was evaluated by the number of tumour-free rats after 3, 6 and 13 weeks respectively. The treated rats demonstrated a significant reduction in tumour outgrowth compared both to untreated controls and to animals treated with the histamine H2-antagonist alone.

TABLE

Stimulation of NK activity of human mononuclear blood cells by plasma of blood samples incubated with various doses of PHA for 4 hours at 37° C.

| Preincubation of effector cells | | Specific $^{51}$Cr release at ratio | | | lytic units[1] |
|---|---|---|---|---|---|
| Type of plasma | Dilution | 20:1 | 10:1 | 5:1 | per $10^7$ |
| Medium | — | 33.2 | 10.8 | 8.2 | 9.9 |
| Plasma control | 1:100 | 38.1 | 28.6 | 20.1 | 18.4 |
| Plasma of blood +32 ug PHA-LS[2] | 1:100 | 38.8 | 35.3 | 15.1 | 19.7 |
| Plasma of blood +8 ug PHA-LS[2] | 1:100 | 47.6* | 41.9* | 30.3* | 44.3 |
| Plasma of blood +2 ug PHA-LS[2] | 1:100 | 48.9* | 32.1 | 23.3 | 25.9 |
| Plasma of blood +0.5 ug PHA-LS[2] | 1:100 | 39.4 | 26.4 | 19.2 | 17.8 |
| Plasma of blood +0.13 ug PHA-LS[2] | 1:100 | 36.8 | 24.4 | 15.6 | 15.2 |
| Medium | — | 33.2 | 10.8 | 8.2 | 9.9 |
| Plasma control | 1:30 | 43.4 | 33.7 | 22.9 | 25.1 |
| Plasma of blood +32 ug PHA-LS | 1:30 | 46.4 | 32.9 | 15.5 | 21.5 |
| Plasma of blood +8 ug PHA-LS | 1:30 | 25.1 | 24.0 | 12.9 | 6.9 |
| Plasma of blood +2 ug PHA-LS | 1:30 | 67.5** | 49.1** | 29.1 | 39.0 |
| Plasma of blood +0.5 ug PHA-LS | 1:30 | 33.4 | 28.2 | 25.7 | 17.0 |
| Plasma of blood +0.13 ug PHA-LS | 1:30 | 40.5 | 31.8 | 23.4 | 23.3 |

[1] One lytic unit is the number of effector cells required to result in 30% specific $^{51}$Cr-release.
[2] Blood was incubated with the indicated amount of PHA per ml for 4 hrs at 37° C. Plasma seperated by centrifugation was ultrafiltered to remove PHA.
\* = $p < 0.05$ in Student's t-test.
\*\* = $p < 0.01$ in Student's t-test.

What we claim is:

1. A method of treating interferon sensitive diseases, comprising the steps of taking a whole blood sample from a human or animal patient suffering from such disease, incubating said whole blood sample in vitro in the presence of a mitogen to produce γ-interferon, subjecting said incubated whole blood sample to a separation step so as to produce a blood plasma preparation which is free of said mitogen but contains a therapeutically effective amount of said produced γ-interferon, and re-administering said blood plasma preparation to the same patient.

2. The method of claim 1, wherein said separation step comprises centrifugation of said incubated whole blood sample for separating the blood plasma, and ultrafiltration of said blood plasma for removing said mitogen therefrom.

3. The method of claim 1, wherein said blood plasma preparation is readministered to the patient by injection.

4. The method of claim 1, comprising the step of simultaneously administering to the patient a therapeutically effective amount of a histamine H2-antagonist.

5. The method of claim 1, wherein said incubation of said whole blood sample also produces at least one lymphokin other than interferon, and wherein said separation step is carried out so as to retain at least a major part of said at least one lymphokin in said plasma preparation.

6. The method of claim 5 wherein the lymphokin other than interferon is interleukin II.

* * * * *